(12) United States Patent
Nordquist

(10) Patent No.: US 7,507,253 B2
(45) Date of Patent: Mar. 24, 2009

(54) IMPLANTABLE BRACE FOR A FRACTURE AND METHODS

(76) Inventor: William D. Nordquist, 2304 6th Ave., San Diego, CA (US) 92101

( * ) Notice: Subject to any disclaimer, the term of this patent is extended or adjusted under 35 U.S.C. 154(b) by 433 days.

(21) Appl. No.: 10/952,936

(22) Filed: Sep. 30, 2004

(65) Prior Publication Data

US 2005/0090900 A1 Apr. 28, 2005

Related U.S. Application Data

(60) Provisional application No. 60/513,349, filed on Oct. 22, 2003.

(51) Int. Cl.
- A61F 2/28 (2006.01)
- A61F 5/00 (2006.01)
- A61B 17/80 (2006.01)
- A61B 17/88 (2006.01)

(52) U.S. Cl. ............. 623/16.11; 623/17.11; 623/17.16; 606/280; 606/281; 606/86 R

(58) Field of Classification Search ............. 623/16.11, 623/17.11–17.16, 23.71, 23.72, 23.73, 23.74, 623/23.75, 23.76, 11.11; 606/60–62, 69–73, 606/280, 281, 86 R, 282–302, 297, 902–916
See application file for complete search history.

(56) References Cited

U.S. PATENT DOCUMENTS

| | | | | |
|---|---|---|---|---|
| 2,133,859 A * | 10/1938 | Hawley | | 606/281 |
| 2,614,559 A * | 10/1952 | Livingston | | 606/64 |
| 3,720,959 A * | 3/1973 | Hahn | | 623/17.17 |
| 3,849,805 A * | 11/1974 | Leake et al. | | 623/17.17 |
| 4,211,228 A * | 7/1980 | Cloutier | | 606/102 |
| 4,636,215 A * | 1/1987 | Schwartz | | 623/17.17 |
| 4,787,906 A * | 11/1988 | Haris | | 623/23.72 |
| 4,790,302 A * | 12/1988 | Colwill et al. | | 606/62 |
| 4,838,252 A * | 6/1989 | Klaue | | 606/280 |
| 5,133,718 A * | 7/1992 | Mao | | 606/281 |
| 5,503,164 A * | 4/1996 | Friedman | | 128/898 |
| 5,545,226 A * | 8/1996 | Wingo et al. | | 623/17.19 |
| 5,700,267 A * | 12/1997 | Urbanski | | 606/86 R |
| 5,968,046 A * | 10/1999 | Castleman | | 606/286 |
| 6,176,879 B1* | 1/2001 | Reischl et al. | | 623/11.11 |
| 6,350,284 B1* | 2/2002 | Tormala et al. | | 623/17.19 |
| 6,454,770 B1* | 9/2002 | Klaue | | 606/281 |
| 6,491,725 B1* | 12/2002 | Koyama et al. | | 623/17.19 |
| 6,585,739 B2* | 7/2003 | Kuras et al. | | 606/301 |
| 6,626,945 B2* | 9/2003 | Simon et al. | | 623/17.19 |
| 6,696,073 B2* | 2/2004 | Boyce et al. | | 424/422 |
| 7,037,342 B2* | 5/2006 | Nilsson et al. | | 623/21.15 |
| 7,113,841 B2* | 9/2006 | Abe et al. | | 700/118 |
| 7,351,058 B2* | 4/2008 | Fore et al. | | 433/18 |
| 7,425,213 B2* | 9/2008 | Orbay | | 606/62 |
| 2005/0288790 A1* | 12/2005 | Swords | | 623/17.19 |
| 2006/0224242 A1* | 10/2006 | Swords et al. | | 623/17.19 |
| 2008/0228278 A1* | 9/2008 | Lee et al. | | 623/17.17 |

* cited by examiner

Primary Examiner—Alvin J Stewart

(57) ABSTRACT

An implantable brace for immobilizing a fracture and promoting osteogenesis is placed in an osteotomy. The implantable brace may be preformed or made by a method in which the implantable brace is cast from a three-dimensional model of a patient's fractured bone in which a model osteotomy designed by a surgeon has been cut. In a method for implanting the brace in a patient, an osteotomy is formed in the patient's bone to receive the implantable brace.

10 Claims, 9 Drawing Sheets

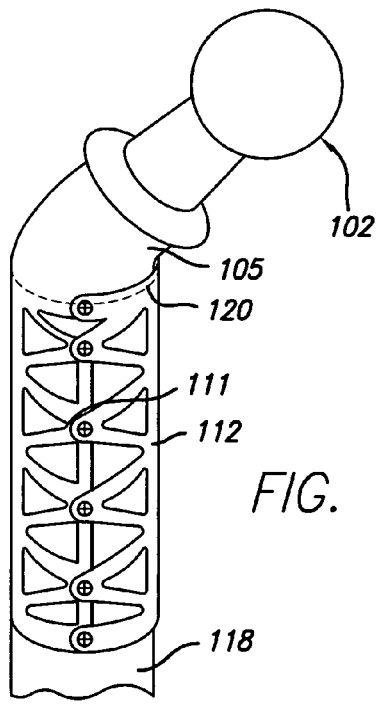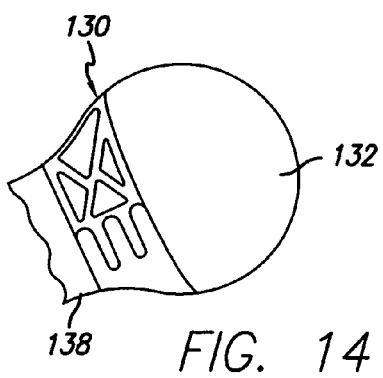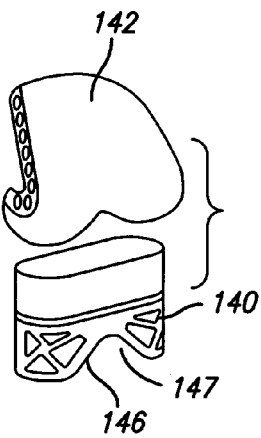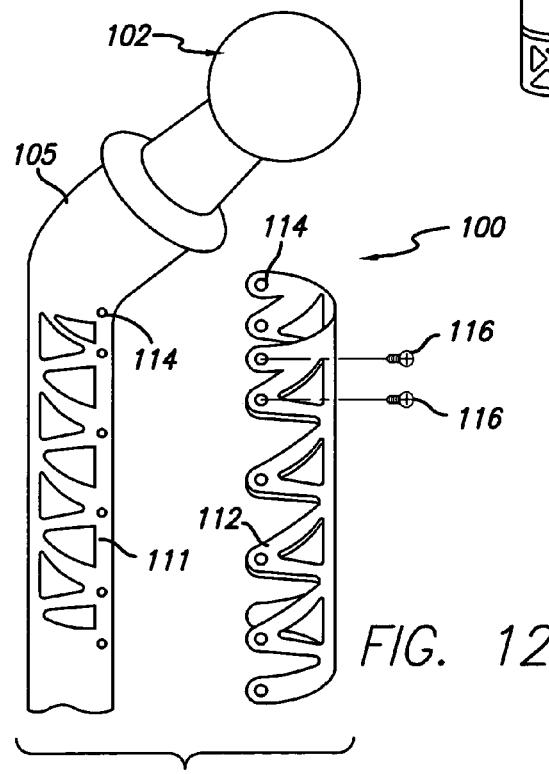

IMPLANTABLE BRACE FOR A FRACTURE AND METHODS

CROSS REFERENCE TO RELATED APPLICATIONS

This application claims the benefit of U.S. Provisional Patent Application 60/513,349 filed Oct. 22, 2003, the contents of which are incorporated herein by reference in their entirety.

FIELD OF THE INVENTION

The present subject matter relates to an implantable brace for immobilizing a fracture and promoting osteogenesis, as well as to methods for making the brace and to methods for implanting the brace in a patient.

BACKGROUND OF THE INVENTION

A common method for treatment of a bone fracture is to align portions of a bone that are separated by a fracture in a fixed spatial relationship. Generally, as the bone regenerates, the fractured portions of the bone will "knit," and the fracture will be healed. Accordingly, simple fractures are often merely splinted while the fracture heals. In the case of serious fractures, medical devices may be employed to provide arthrodesis, or the surgical immobilization of a joint so that fractured bones grow together solidly.

A bracing device can be used in various arrangements to maintain the alignment of portions of a fractured bone. For example, a bracing device may be affixed to a portion of a bone with one or more surgical screws. Such use of surgical screws is a common practice in treatment of stress fractures in horses. A stress fracture is a prevalent form of injury to race horses that is not readily detectable by radiography. Often, stress fractures occur approximately ⅔ of the way from the knee to the fetlock joint of the horse's leg. The cannon bone may have a smaller diameter at this location than at other locations. A stress fracture is often detected as a density, or bump, overlaying the cortex of the cannon bone. The bump is due to new bone which is being laid down over the top of the fracture (callous formation) in an attempt by the horse's body to repair the injury.

Accordingly, prior art structures using surgical screws will, of necessity, cause contact of medical device components with soft tissue and muscles overlying the bone. As such, the requisite external device components, for example rods and plates, can often irritate the soft tissue and muscle. This irritation may cause either human or animal patients to suffer from chronic pain. However, devices requiring fixation to the bone do not provide a way to avoid contact with the surrounding tissue.

In this regard, U.S. Pat. No. 6,355,041 describes one prior art device for veterinary use for fetlock joint breakdown. A first end of the disclosed pin-plate device is a pin received in a bore formed in a center of a horse's third metacarpal bone, also known as the cannon bone. This is the horse's lower leg bone. A second end of the device is a plate affixed to a rear exterior surface of a first phalanx by surgical screws extending through the plate into the first phalanx. The first phalanx is a bone above the horse's hoof. The plate and the surgical screws contact surrounding tissue. Such contact is undesirable.

Another problem encountered with prior art bracing devices is "stress shielding." Stress shielding is the loss of bone that occurs when stress is diverted from an area of bone. Bones tend to atrophy when they are unloaded. In natural body functioning, calcium is often lost from the bone where it is not needed for strength, resulting in a reduction in bone mass. Many prior art brace arrangements cause such stress shielding. For example, a steel rod brace inserted lengthwise in the center of a bone is many times stronger than the resulting bone surrounding it and thus removes some of the load from the bone. Consequently, there is an unequal sharing of the load between the steel rod and the bone, resulting in stress shielding of the bone. Such stress shielding is a major cause of failures in, for example, hip prosthesis surgery, as a steel rod inserted in the femur absorbs loading and leads to weakening of the femur.

There has been recognition in the art of the cause and effects of stress shielding. One suggested prior art technique to avoid this cause utilizes a hip prosthesis without a stem. Likewise, in the case of orthopedic fixation, it was noticed that screws that were significantly harder than bone could loosen. In addition to jeopardizing the healing process, this phenomenon could endanger adjacent anatomical structures. Accordingly, it has previously been suggested to use titanium screws since titanium has a level of flexibility reasonably close to that of bone and will transmit stress to a bone. However, there has not been great emphasis in providing natural loading of the bone with a device implanted therein. Limited progress has been made with respect to simulating normal load bearing in a surgically braced bone.

Another difficulty is that many previous schemes providing for arthrodesis do not allow normal patient functioning with a brace in place. This problem has been particularly difficult in veterinary practice since patients cannot be encouraged to stay still. One such example is equine fractures that are more severe than stress fractures. When a horse breaks the fetlock joint, or more particularly, the metacarpal-phalangeal joint, for example, a breakdown in supporting structures of the fetlock joint leaves a horse unable to support its weight. In many such cases, the horse previously could not be provided with a suitable bracing structure to permit healing of the supporting structures while still enabling the horse to walk or stand normally. The horse would thus be unable to continue normal functioning. Traditionally, this type of injury has often resulted in the killing of the horse.

More recently, treatments have been provided to stabilize the fetlock joint through arthrodesis. However, complications have often followed arthrodesis. Typical complications include support limb laminitis, infection, implantation failure, and cast sores. Even when the treatment is ultimately successful, however, the horse typically does not regain normal leg function. This is because many of these previous treatments fuse the fetlock joint into an unnatural straight line, resulting in an extended limb length. This difference in limb length can cause a horse to overload its pastern and coffin joints, which are in the vicinity of the hoof. The overload can in turn lead to degenerative joint disease and pastern joint subluxation. The bones of the fetlock joint do not resume their original relative positions. Accordingly, while the horse may still be saved for breeding, it usually is unable to perform any other traditional functions.

In the treatment of humans, there are many previously known techniques for holding adjacent sections of a fractured bone together. One such technique is the insertion of pins. Often, however, additional surgery is needed for removal of these pins after a particular degree of bone regrowth has occurred. Another previous technique is the implantation of a plate to which bones must be affixed. However, the plate often provides a structure that does not duplicate the original shape of the bone. Casts are also commonly used to protect and stabilize fractures. Casts have the downside of greatly reducing the mobility of a patient, as well as causing sores and other irritation and great difficulty in bathing and other day-to-day tasks. Accordingly, it is highly desirable to avoid these prior shortcomings.

In this regard, U.S. Pat. No. 6,613,049 discloses a bone stabilizing frame system in which upper and lower clamping members are affixed to a bone on opposite sides of a fracture. External rods maintain the upper and lower clamps in a fixed spatial relationship. The size and location of the rods reduce the capability of a patient to function normally while healing in comparison to a stabilizing structure that would fit within a bone. However, this disclosed system has not been shown to be effective in practice.

Another example of an area in which difficulty has been encountered in tailoring available treatment procedures to avoid some of these traditionally encountered problems is spinal fusion. A common form of spine injury is herniation or other damage to intervertebral disks. Discs can compress against nerves in the spinal column and cause a high level of pain. Commonly, an entire vertebral disc is removed from between adjacent upper and lower vertebrae. The upper and lower vertebrae are fused to form a single spinal structure. Many forms of spinal fusion procedures have a low success rate, e.g., 40%. It is important to provide a procedure that fosters fusion between the vertebrae while maintaining a desired distance between the vertebrae adjacent the removed disc.

Accordingly, the current solutions for bracing bone fractures do not address in a flexible manner the need to provide relatively normal bone loading, minimal interference with muscle and soft tissue, and promotion of osteogenesis. The present subject matter addresses these needs.

SUMMARY OF THE INVENTION

An apparatus and method are provided herein to aid bones on opposite sides of a fracture return to their original juxtaposition. These apparatuses and methods are capable of providing a stable, post-fracture structure, wherein functioning of a healed joint is not lost. As such, the present subject matter will allow race horses in many cases be able to return to racing. Additionally, in many situations humans will also be able to be treated without the need for pins, plates, or casts.

The present subject matter provides for the ability to address a wide variety of situations in which it is desired to provide for substantially normal loading on a bone and minimize interference with muscle and soft tissue. For example, the implantable brace herein can also be combined with a prosthetic component. For particular applications, the brace is configurable to provide secure fixation to a bone while avoiding ligaments. The brace can also be configured for applications to provide for arthrodesis.

In a preferred embodiment, the present subject matter relates to an implantable brace comprising at least one structural member having portions to align first and second bone portions. This structural member defines an envelope to fit within a bone recess defined by an osteotomy. The structural member is formed to have a surface that enables integration with bone produced by osteogenesis within the osteotomy.

In another preferred embodiment, the present subject matter relates to a method for forming an implantable brace implantable in a fractured bone of a patient comprising making a model of a fractured bone of a patient; forming an osteotomy design and an osteotomy pattern for the model, the osteotomy design having a depth to receive an envelope of the implantable brace and the osteotomy pattern having a shape to permit implantable portions of the implantable brace to be inserted in an osteotomy without conflict with tissue position; cutting the osteotomy design into the model to form an osteotomy model; and forming the implantable brace by using the osteotomy model.

In yet another preferred embodiment, the present subject matter relates to a method for implanting an implantable brace in an osteotomy in a bone comprising providing a preformed implantable brace comprising an open framework structure having a contour approximating a contour of a preselected bone; forming an osteotomy in the bone to a depth to receive the implantable brace below a surface of said bone; manipulating tissue adjacent to the bone to permit placement of said implantable brace in said osteotomy; and placing said implantable brace in said osteotomy.

BRIEF DESCRIPTION OF THE DRAWINGS

The present subject matter is further understood by reference to the following drawings taken in connection with the following description.

FIG. 12 is an exploded view of a multipart brace incorporating a prosthetic component;

FIG. 13 is an illustration of the embodiment of FIG. 12 assembled;

FIG. 14 is an illustration of another form of implantable brace incorporating a prosthetic component;

FIG. 15 is an illustration of a further form of implantable brace incorporating prosthetic components and formed for installation to avoid interference with ligaments;

DETAILED DESCRIPTION

Figure 1A:
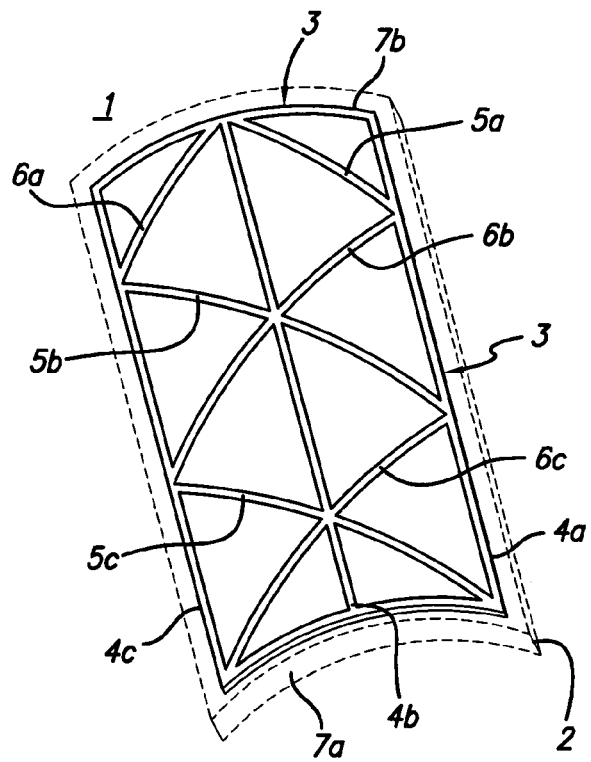
FIG. 1, consisting of FIGS. 1a, 1b and 1c, illustrates a unitary implantable brace, an envelope defining a volume in which the implantable brace fits and a multipart implantable brace, respectively.
Figure 1B:
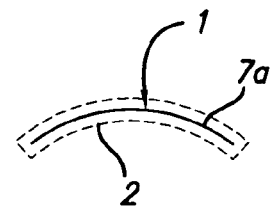
Figure 1C:
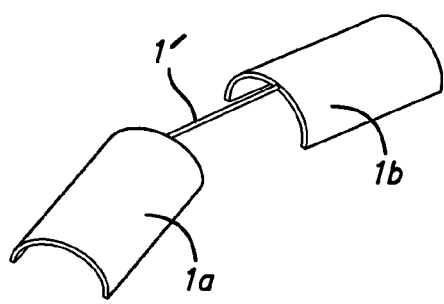

An implantable brace of the present subject matter can be described with reference to FIG. 1, consisting of FIGS. 1a, 1b and 1c, which illustrate a unitary implantable brace, an envelope defining a volume in which the implantable brace fits, and a multipart implantable brace, respectively. The solid lines represent the implantable brace 1. The dotted lines represent an envelope 2, which is a volume in which the implantable brace 1 will fit. The implantable brace 1 is particularly adapted to fit within an osteotomy, i.e. a network of recesses cut into a bone by a surgeon.

The implantable brace 1 is has a surface that enables integration with bone produced by osteogenesis within the osteotomy. In one preferred form, the entire surface of the implantable brace 1 is formed in this manner. However, in other forms, portions of the surface of the implantable brace 1 may be formed in this manner. Surface treatment to enable bone intergration is known in the art, for example with respect to prosthetics mounted on a stem which is implanted in a bore in a bone and also with respect to dental implants. The surface may, for example, be either grit blasted and/or etched, coated with hydroxyapatite (HA), fluorapatite (FA) or other known suitable coating. The implant surface facilitates the adhesion of osteoblast precursor cells. Osteoblasts then deposit, and the known sequence of formation of osteocytes and osteoclasts follows. The implantable brace 1 promotes osteogenesis within the confines of osteotomy. Undesirable bone growth outside of the osteotomy is not promoted.

The implantable brace 1 has an envelope 2 in a shape comprising a portion of an axially extending wall of a right circular cylinder. This shape is particularly suited for bracing fractures extending in both a radial and an axial degree of freedom in a bone having an axial length. Examples of this type of bone are the human femur and the equine cannon, or third metacarpal bone. The implantable brace 1 may be shaped to fit within other types of bones as well. The implantable brace 1 could also be fit between a plurality of bones spaced from each other. The implantable brace 1 could be unitary, as in FIG. 1a, or may comprise sections 1a and 1b linked by a link 1', as in FIG. 1c.

The implantable brace 1 in a preferred form may comprise an open framework 3. The open framework 3 has the advantages of providing structural strength and having the ability to fit into a network of recesses comprising an osteotomy. Many different materials may be used for the open framework 3. Titanium is a preferred material because its stiffness is comparable to that of bone, and normal loading of stress on the bone will be facilitated.

The open framework 3 of the implantable brace 1 is formed from at least one structural member having portions to align first and second bone portions. In a preferred embodiment, the open framework 3 comprises first, second and third structural members 4a, 4b and 4c. These members are substantially parallel, and extend in an axial direction.

In another preferred embodiment, the structural members 4a, 4b and 4c are braced by bracing members 5a, 5b and 5c at a first angle to the structural members 4a, 4b and 4c, preferably 45°. Bracing members 6a, 6b and 6c are preferably perpendicular to the bracing members 5a, 5b and 5c and at an angle of 45° to the structural members 4a, 4b and 4c. Intersections of the bracing members 5a, 5b and 5c with the structural members 4a, 4b and 4c overlap intersections of the structural members 4a, 4b and 4c with the bracing members 6a, 6b and 6c.

In a further preferred embodiment, a first circumferential member 7a is joined to first ends of the structural members 4a, 4b and 4c. A second circumferential member 7b is joined to second ends of the structural members 4a, 4b and 4c. In this embodiment, the components thus described form a lattice, i.e. an open framework with a regular pattern.

Figure 2:
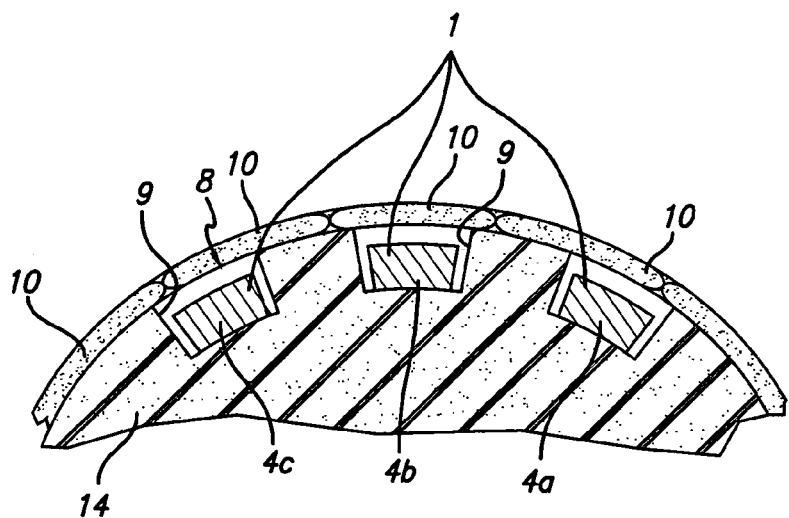
FIG. 2 is a cross section of an implantable brace placed in a recess defined by an osteotomy.

FIG. 2 shows a cross section of a preferred implantable brace placed in a recess defined by an osteotomy 8. The term "osteotomy" is commonly used in the art to refer both to the process of cutting bone and the recess produced by the process. In the present embodiment, the osteotomy 8 is cut into a bone 14, and comprises a series of channels 9. The channels 9 are formed in a pattern further described below with respect to FIGS. 3-5. The osteotomy 8 defines a recess to receive the implantable brace 1. Commonly, tissue 10 will be present over the bone 14. Depending on the location in the body the tissue 10 will comprise one or more of muscle, cartilage or other tissue. Manipulation of the tissue 10 may be required in order for a surgeon to place the implantable brace 1 in the osteotomy 8. The osteotomy 8 is designed so that the envelope 2 of the implantable brace 1 fits within the recess defined by the osteotomy 8. Consequently, the implantable brace 1 will not engage or irritate the tissue 10. It should be noted that the implantable brace 1 generally will not fill the osteotomy 8 completely. In the absence of other procedures, blood will fill the open areas. The blood will eventually turn to bone. To promote orderly healing it is preferable to place augmentation material such demineralized, freeze dried bone, resorbable or non-resorbable hydroxyapatite or other osseous combinations mixed with whole blood, plasma, or platelet rich plasma.

Figure 3:
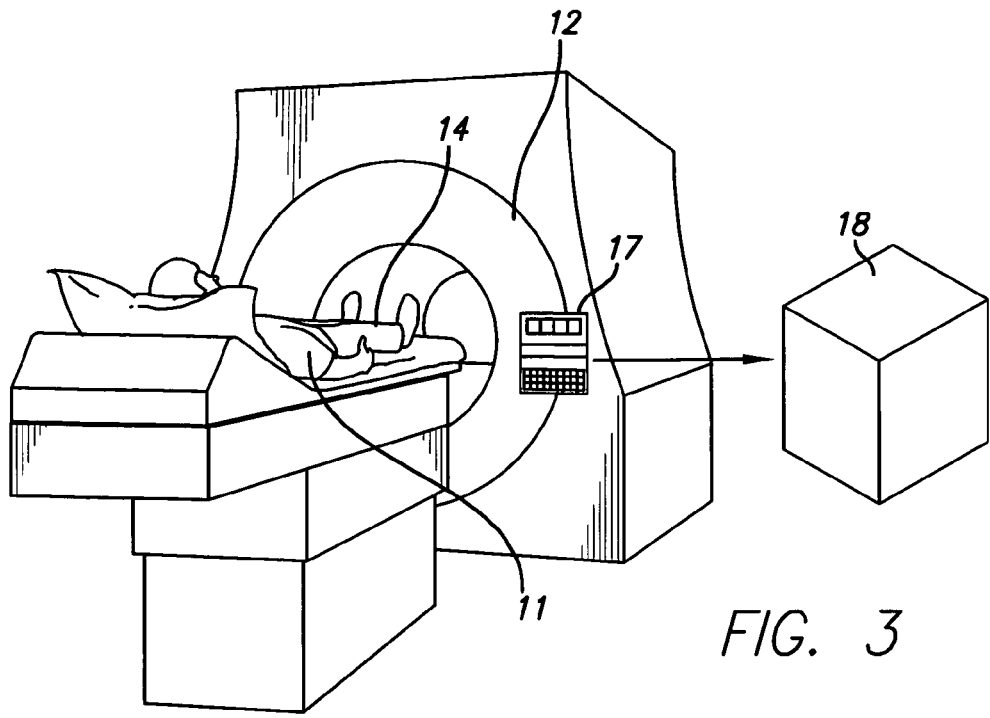
FIG. 3 is an illustration of a patient undergoing a CAT scan.

The implantable brace 1 may be preformed or may be custom made for a particular fracture. In one preferred form, a model of the fracture bone is made. The model will be used by a surgeon as further described below. Data is gathered on which construction of a model is based. A preferable way to gather data using current technology is to perform a CAT (computerized axial tomography) scan of a fractured bone. Data produced by the CAT scan is used for making a three-dimensional model of a portion of a bone on which a surgeon will operate. In a preferred embodiment, a stereo lithography model is produced from the CAT scan data. In this regard, FIG. 3 illustrates a preferred embodiment wherein a patient 11 is scanned in a CAT scanner 12. By scanning the patient 11 in two dimensions in each of a large number of successive planes, the CAT scanner 12 produces a three-dimensional image of a scanned portion of the patient 11.

In the example of FIG. 3, the patient 11 has a broken bone 14. In this example, the bone 14 is the femur. Once the patient's leg is scanned, output data is produced indicative of a three-dimensional image of the fractured bone 14. This data may be stored in a memory of a computer 17, and provided to a stereo lithography machine 18, also known as a three-dimensional printer. Other well-known data handling means may be used, such as coupling the CAT scanner 12 to a network rather than to a dedicated local computer.

In a well-known manner, in the stereo lithography machine 18, a laser (not shown) traces a path through a light-sensitive resin for each layer of the image in order to produce a three dimensional model 15 of the fractured bone 14. Other forms of three-dimensional printing, such as processing of powders to produce a three-dimensional solid, are contemplated as useful herein. A design for an implantable brace is then drawn into the model surface.

Figure 4:
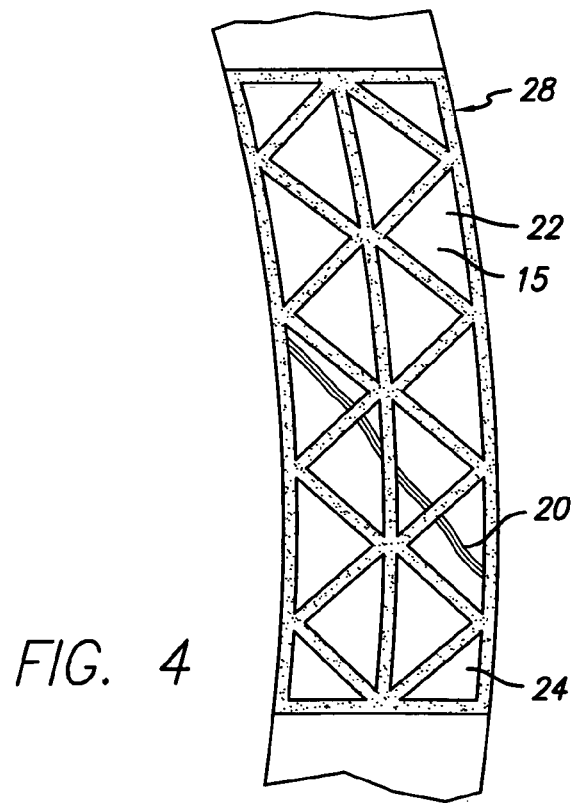
FIG. 4 illustrates the model of a fractured bone with a design for an implantable brace drawn thereon.
Figure 9:
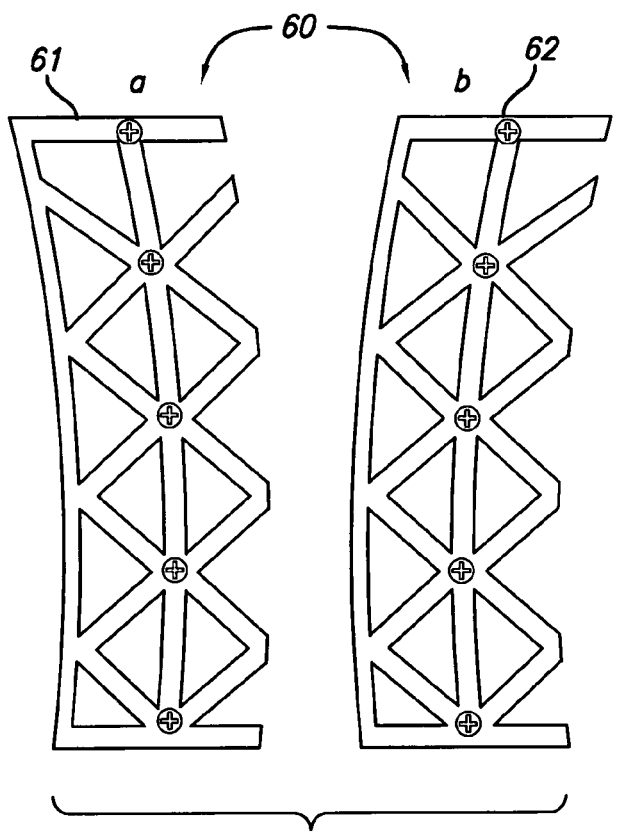
FIG. 9, consisting of FIG. 9a and FIG. 9b, illustrates a cast implantable brace.

FIG. 4 illustrates the model of a fractured bone with a design for an implantable brace drawn thereon. For simplicity of the drawing, a smooth fracture 20 is shown in an idealized form. The fracture 20 separates an upper bone portion 22 from a lower bone portion 24. The surgeon arranges the upper and lower bone portions 22 and 24 into the juxtaposition in which they will be operated upon. The surgeon then plans a design 28 of a structure for bracing the bone portions 22 and 24 so they will knit properly. The pattern 28 is formed to have a shape to permit implantable portions to be inserted in the osteotomy without conflict with the position of tissue 10. Conflict will occur if the required degree of manipulation of tissue 10 is greater than the degree of manipulation of which the tissue 10 is capable. This structure can be the implantable brace 60 of FIGS. 9 and 11 below. In a preferred embodiment, the surgeon may draw the design 28 of the brace directly on the model 15, as illustrated in FIG. 4.

Figure 5A:
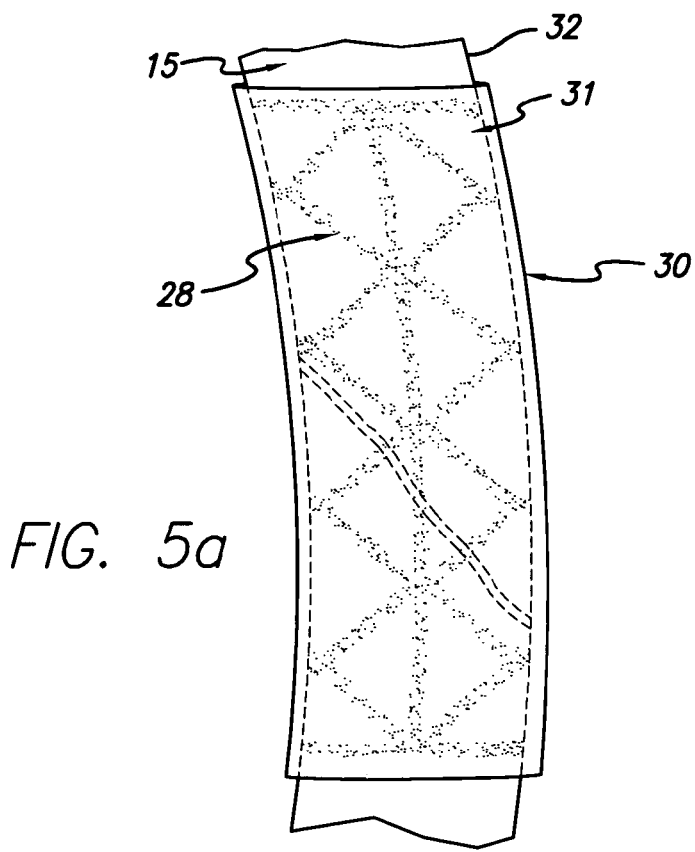
FIG. 5a illustrates a transfer template made to fit over the area of a bone model where the implantable brace is to be constructed.
Figure 5B:
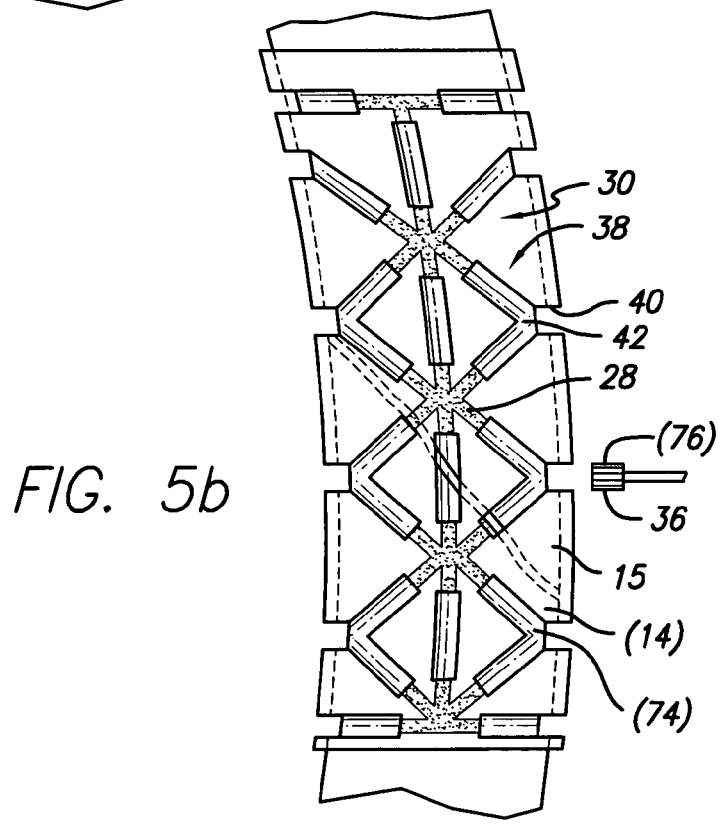
FIG. 5b is an illustration of the transfer template of FIG. 5a fit over a patient's bone model or bone and illustrating a rotary cutting instrument which cuts to the desired osteotomy depth.

FIG. 5a illustrates a transfer template 30 made to fit over the area of a bone where the implantable brace 1 is to be placed. The transfer template 30 transfers the design for the implantable brace 1 onto a bone. FIG. 5b is an illustration of the transfer template of FIG. 5a fit over a patient's bone model or bone and illustrating a rotary cutting instrument which cuts to the desired osteotomy depth. In a preferred embodiment, the design 28 can be applied to the transfer template 30. The application may be done by tracing, by a photographic process, or by any other technique commonly known to those of skill in the art. The transfer template 30 is then placed over the model 15. The transfer template 30 may comprise first and second arcuate portions 31 and 32, each covering approximately one half of the circumference of a bone.

The transfer template 30 may be made of a number of different materials including but not limited to clear plastic, metal, and radiologic film. In a preferred embodiment, the transfer template 30 is made of radiologic film. Radiologic film is clear, allowing for ready transfer of the pattern 28. Additionally, radiologic film will withstand sterilization. In an alternative preferred embodiment, the transfer template 30 comprises a thin metal material, which is also sterilizable.

FIG. 5b illustrates the formation of a pattern 38 in the transfer template 30. The reference numerals in FIGS. 5b and 7 that are in parentheses are discussed with respect to FIG. 11 below. The pattern 38 is in effect a stencil from which the pattern 28 may be reproduced. This pattern 38 will correspond to vertices and extremities of the pattern 28. The complete pattern 28 is not cut in the transfer template 30 since holes would be created. In a preferred form, the transfer template 30 comprises portions of a design which convey sufficient information so that a surgeon can complete cutting of the design into the patient's bone 14 after the transfer template 30 is removed.

In a preferred embodiment, a cutting tool 36, for example a square rotary carbide burr, is used to cut grooves 40 into the transfer template 30 to a desired osteotomy depth. In alternative preferred embodiments, the grooves 40 can be cut into the transfer template 30 by other mechanical means or by a laser. The grooves 40 taken together comprise the pattern 38. While forming the grooves 40 through the transfer template 30, the cutting tool 36 also cuts into the model 15 to create grooves 42. The transfer template 30 is then removed from the model 15, allowing a surgeon to connect the grooves 42 to complete the osteotomy pattern 28 in the model 15.

Figure 6:
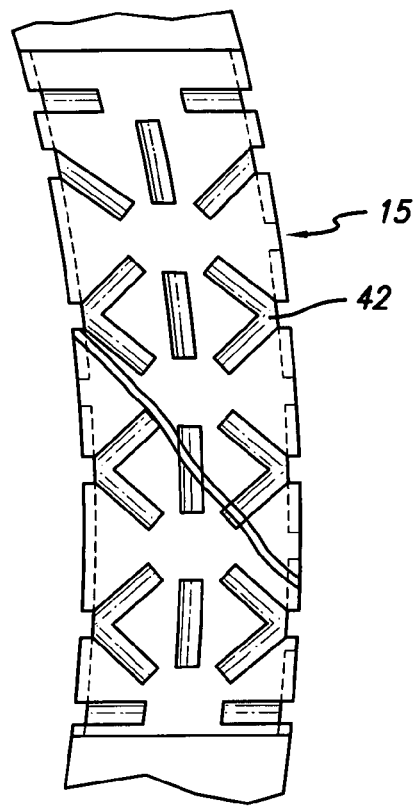
FIG. 6 illustrates a partially completed model osteotomy with the transfer template removed.

FIG. 6 is an illustration of the model 15 with the transfer template 30 removed therefrom. The model 15 is further worked as described with respect to FIG. 7, which illustrates completion of an osteotomy in the model 15. The grooves 42 define a definite path. The grooves 42 are connected to complete a network seen in FIG. 7 corresponding to the pattern 28. The model 15 now comprises a model of a bone 14 prepared for placement of an implantable brace 1. A custom made implantable brace 1 may be constructed using the model 15.

The implantable brace 1 may be made by any fabrication method commonly known to those skilled in the art. One well-known, preferred technique for producing an article to fit a model is investment casting.

Figure 8:
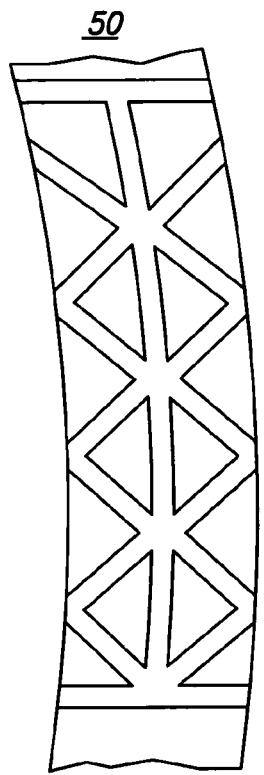
FIG. 8 is an illustration of investing of the wax impression produced by the process of FIG. 7.

In particular, a wax model can be made in the osteotomy. It is then invested. More specifically, the wax model is preferably dipped in a ceramic slurry and then coated with a refractory grain until a shell is formed. The wax is melted out of the shell mold. The casting is then made in the shell mold. In a situation in which a long bone, such as a femur or canon bone, needs to be splinted, the cast can be made out of a plurality of components that are fastened together. Carpus or sesamoid bones may be splinted with a one-sided plate that is screw fastened to the bone. The apparatus, once cast, is then finished, and the surface is either grit blasted and/or acid etched, coated with hydroxyapatite (HA), fluorapatite (FA) or other known suitable coating. Placement of wax 48 in the grooves 42 is shown to illustrate performance of the investment casting process. A wax model 50 is produced as illustrated in FIG. 8. Other forms of fabrication than casting could be utilized to prepare the implantable brace 1 herein. For example, machining or other manufacturing methods could be performed.

Figure 10:
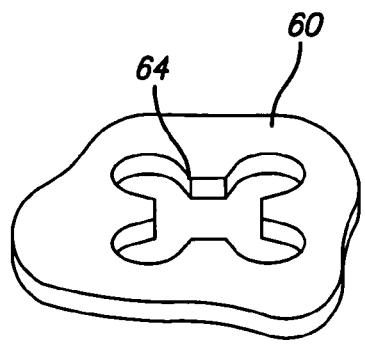
FIG. 10 is a partial detailed view of FIG. 9b and illustrates a screw seat formed in the implantable brace.

FIGS. 9a and 9b are elevations of the first and second portions 61 and 62 of an implantable brace 60 produced by use of the transfer template sections 31 and 32 respectively. FIG. 10 is a partial detailed view of FIG. 9b and illustrates a screw seat 64 formed in the implantable brace 60. The screw seat 64 is designed with an open area to allow bone to grow into the screw seat 64. Consequently, formation of dead space around screw seat 64 is prevented. Dead space can provide an area for the development of bacterial infection.

Figure 7:
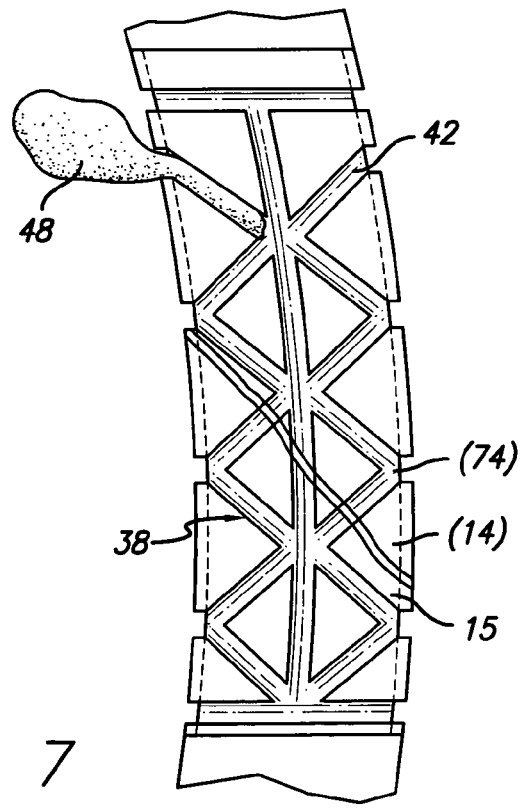
FIG. 7 illustrates completion of an osteotomy in a model and on a patient, as well as placing of wax in the model osteotomy.
Figure 11:
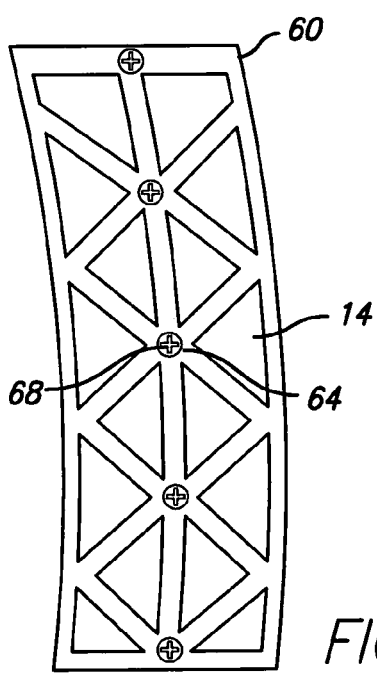
FIG. 11 illustrates installation of the implantable brace in the osteotomy.

FIG. 11 illustrates an implantable brace 60 installed on a bone 14. A surgical screw 68 extends through the screw seat 64 to secure the implantable brace 60 to the bone 14. A surgical procedure on the fracture patient is followed to implant the implantable brace 60. FIGS. 5b and 7 are illustrative of the surgical procedure but with reference to the reference numerals in parentheses in FIGS. 5b and 7. An incision (not shown) is formed to allow access to the bone 14.

As indicated in FIG. 5b, the sections of the transfer template 30 are placed against the bone 14 and fit over the area of the bone 14 where the implantable brace 60 is to be placed. An osteotomy is performed using a cutting tool 76 that follows grooves 40 in the transfer template 30 to form grooves 74 in the bone 14 that will receive the implantable brace 60. Next, the transfer template 30 is removed. In the manner illustrated in FIG. 7, the grooves 74 are completed. Additionally, synthetic, autogenous or other bone-growth stimulating products may be applied to the grooves 74 and the implantable brace 60. The implantable brace 60 is installed into the osteotomy and fastened into place. After installation of the implantable brace 60, surrounding muscle and soft tissue 10 are reapproximated and replaced to substantially their presurgical positions, and the wound is closed and dressed.

FIG. 12 is an exploded view of an alternative preferred implantable brace 100 comprising an additional component projecting outside the osteotomy. In this embodiment, the additional component is a prosthetic component 102. The prosthetic component 102 comprises a femoral section 105 of a prosthetic hip joint. The implantable brace 100 comprises sections 111 and 112 corresponding respectively to the components 61 and 62 of FIGS. 9a and 9b. The sections 111 and 112 each include apertures 114 through which surgical screws 116 are inserted. Each surgical screw 116 preferably extends through one aperture 114 in the section 111 and one aperture 114 in the section 112. When the sections 111 and 112 are mated, the apertures 114 receiving a surgical screw 116 are in registration. The implantable brace 100 can be implanted on a femur 118. In the example of FIG. 13, the femur 118 is cut off at a line 120. The femur 118 is scanned and modeled in a manner similar to modeling of the bone 14 of FIG. 3. The femoral section 105 may be made, by casting or another method, to fit the femur 118, as are the sections 111 and 112.

FIG. 14 illustrates an alternative preferred implantable brace 130 which may be combined with a femoral head prosthesis 132 and secured to a femur 138 in the above-described manner.

FIG. 15 illustrates a further alternative preferred form of implantable brace 140 combined with a prosthetic component. In this illustration, the prosthetic component is a prosthetic knee joint 142. Prosthetic knee joints such as the knee joint 132 need to be implanted in an area in which ligaments need to interact with the knee joint. This presents the necessity to provide for secure attachment to a bone while avoiding engagement or interference with the ligament. The present embodiment accommodates this requirement by permitting shaping of the implantable brace 140 to have a curved border portion 146 defining a recess 147 in the contour of the implantable brace 140. The recess 147 is located in registration with knee ligaments. Consequently, functioning of the joint 142 is maximized while pain caused to a patient is minimized.

Figure 17:
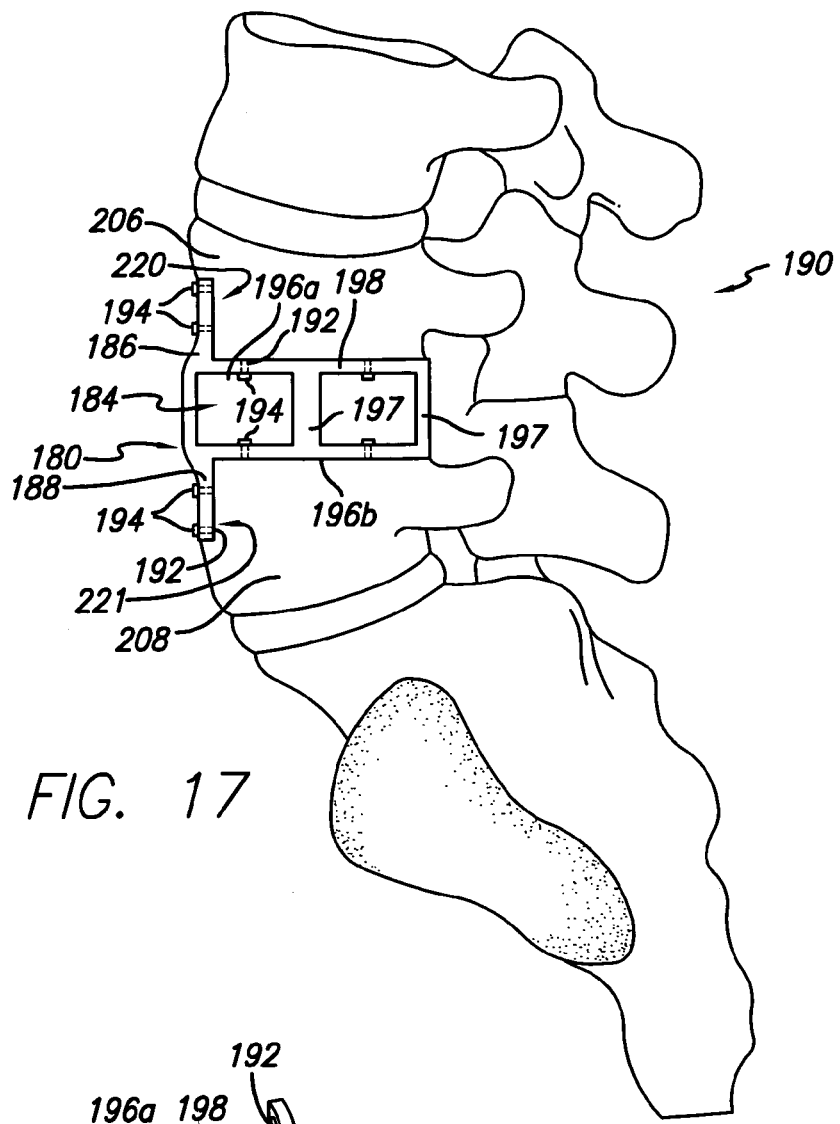
FIG. 17 illustrates the implantable brace of FIG. 16 installed to achieve spinal fusion.
Figure 16:
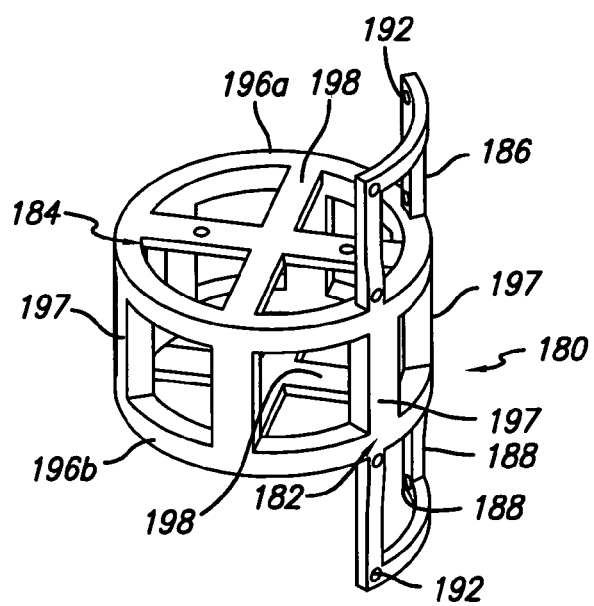
FIG. 16 is an example of an implantable brace suitable to provide for arthrodesis.

FIG. 16 illustrates another alternative preferred form of implantable brace 180. FIG. 17 illustrates the implantable brace 180 implanted in a spine 190. In the present description, the terms upper, lower, horizontal and vertical are comparative rather than absolute. They correspond to orientation within a standing patient. Once again, a patient 11 may receive a CAT scan, as in FIG. 3. The bone structure to be operated upon may be modeled by a stereolithography machine 18. The implantable brace 180 has a linear section 182 supporting a structural frame 184. While the linear section 182 is three-dimensional, it is referred to as linear since its predominant dimension extends in one degree of freedom. Opposite ends of the linear section 182 include an upper anchor section 186 and lower anchor section 188. The implantable brace 180 has apertures 192 through which surgical screws 194 extend. Apertures 192 are also provided in the central structural frame 184.

The structural frame 184 is an open three-dimensional figure designed to fill a particular volume. In the embodiment of FIG. 17, the structural frame 184 is designed to fill a space between two vertebrae in the spine 190 that are to be fused. An upper vertebra 206 and a lower vertebra 208 surround a space that is created due to removal of a defective vertebra and associated cartilage. The structural frame 184 is shaped to fill the space between the upper vertebra 206 and the lower vertebra 208. The structural frame 184 includes upper and lower perimeter forms 196a and 196b defining upper and lower outlines. Vertical struts 197 support the upper and lower perimeter forms 196a and 196b in a fixed spatial relationship. Horizontal struts 198 across each of the upper and lower perimeter forms 196a and 196b comprise members that will bear against adjacent bones and are also fastenable to adjacent bones.

In the present embodiment, osteotomy recesses 220 and 221 are formed in the vertebrae 206 and 208 respectively. The osteotomy recesses 220 and 221 receive the upper anchor section 186 and lower anchor section 188 respectively. Surgical screws 194 are placed through apertures 192 in the upper anchor section 186 and lower anchor section 188. Additionally, since the structural framework 184 is open, surgical screws 194 may also be placed through apertures 194 in the horizontal struts 198 to secure the structural framework 184 to the vertebrae 206 and 208. With this configuration, osteogenesis within the structural frame 184 is enabled. This will result in reliable spinal fusion. This configuration avoids the disadvantages of many prior art systems in which a separator is provided between vertebrae in that no hollow spaces are left between the structural frame 184 and either of vertebrae 206 or 208.

Figure 18:
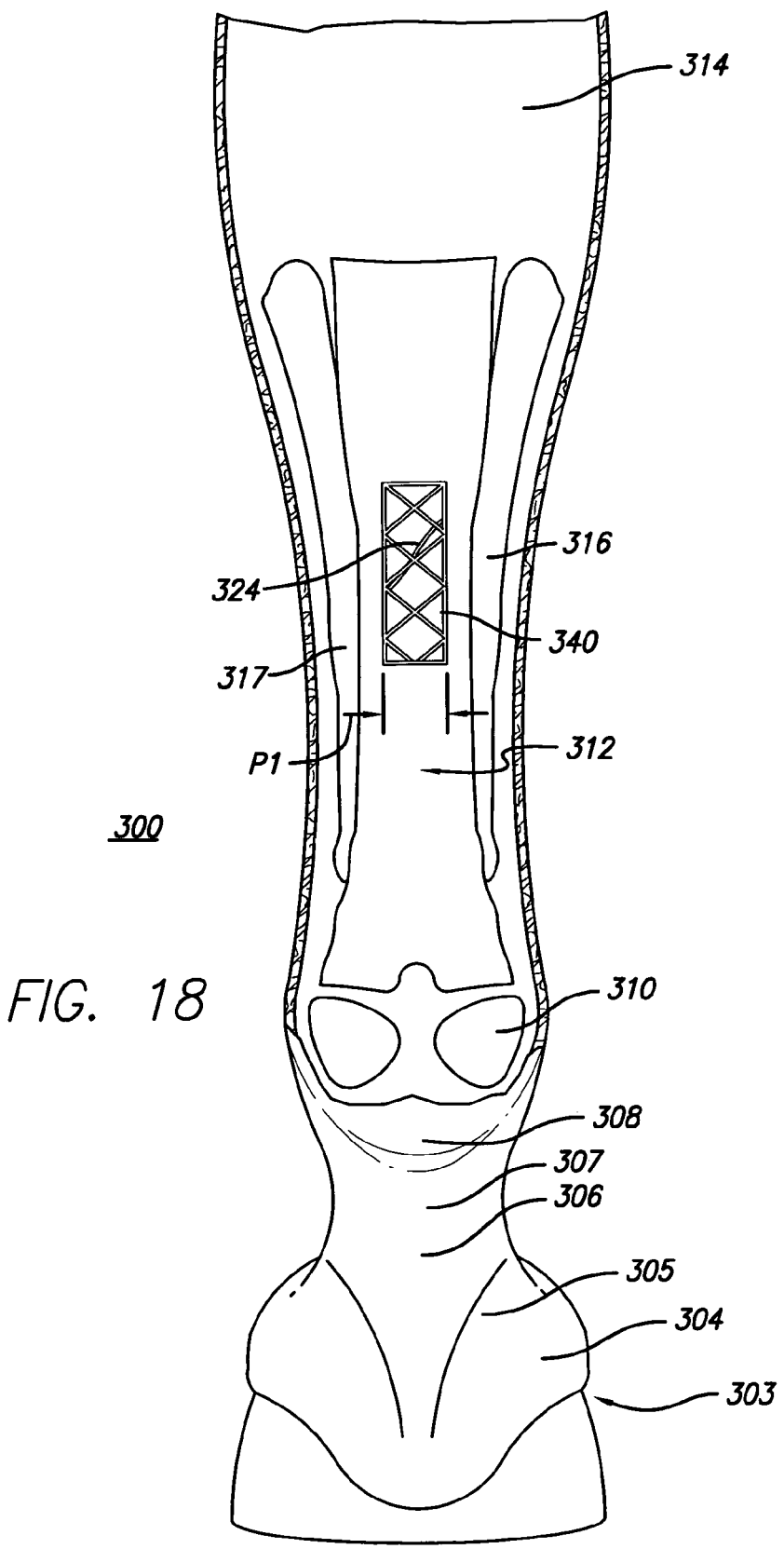
FIG. 18 is an illustration of an equine leg, partially broken away, with a fracture.

FIG. 18 is an illustration of an equine leg 300, partially broken away, with a fracture. A hoof 303 includes a coffin joint 304 connected by a short pastern, or second phalanx, 305 to a pastern joint 306. A long pastern, or first phalanx, 308 extends between the pastern joint 306 and a fetlock joint 310. A cannon bone, or third metacarpal bone, 312 extends between the fetlock joint 310 and a knee 314. A lateral splint bone, or fourth metacarpal bone, 316 and a medial splint bone, or second metacarpal bone, 317 are located on sides of the cannon bone 312. A fracture 324 is illustrated in the cannon bone 312. The implantable brace according to this preferred embodiment is not only useful in treating severe fractures, but is also useful in treating stress fractures.

In FIG. 18, an osteotomy design 340 is illustrated over the fracture 324. The osteotomy needs to have a shape that will maintain portions of the cannon bone 312 in proper alignment. In one embodiment, proper alignment is maintained using the implantable brace 1 of FIG. 1 with three vertical main support beams. The osteotomy design 340 has a fixed, selected width. This width comprises a percentage P1 of the diameter of the cannon bone 312, illustrated in FIG. 18. The same dimension will comprise a different percentage P for a horse having a cannon bone 312 of a differing diameter. P may vary over a range of values while allowing for fit of an implantable brace in a cannon bone 312 to stabilize the fracture 324.

Consequently, in the embodiment of FIG. 18, the implantable brace 1 does not have to be custom made. The implantable brace 1 may be made in "one size fits most." As explained above, many fractures will be in one particular area of the cannon bone 312. Therefore, an implant for that one particular area may only need to take into account variations in sizes of bones at the one vertical location. One size will also accommodate some variation in bone diameter with respect to vertical location on the cannon bone 312. Alternatively, the implantable brace 1 may be made in a number of sizes to approximate dimensions of a custom-made implant.

Figure 19:
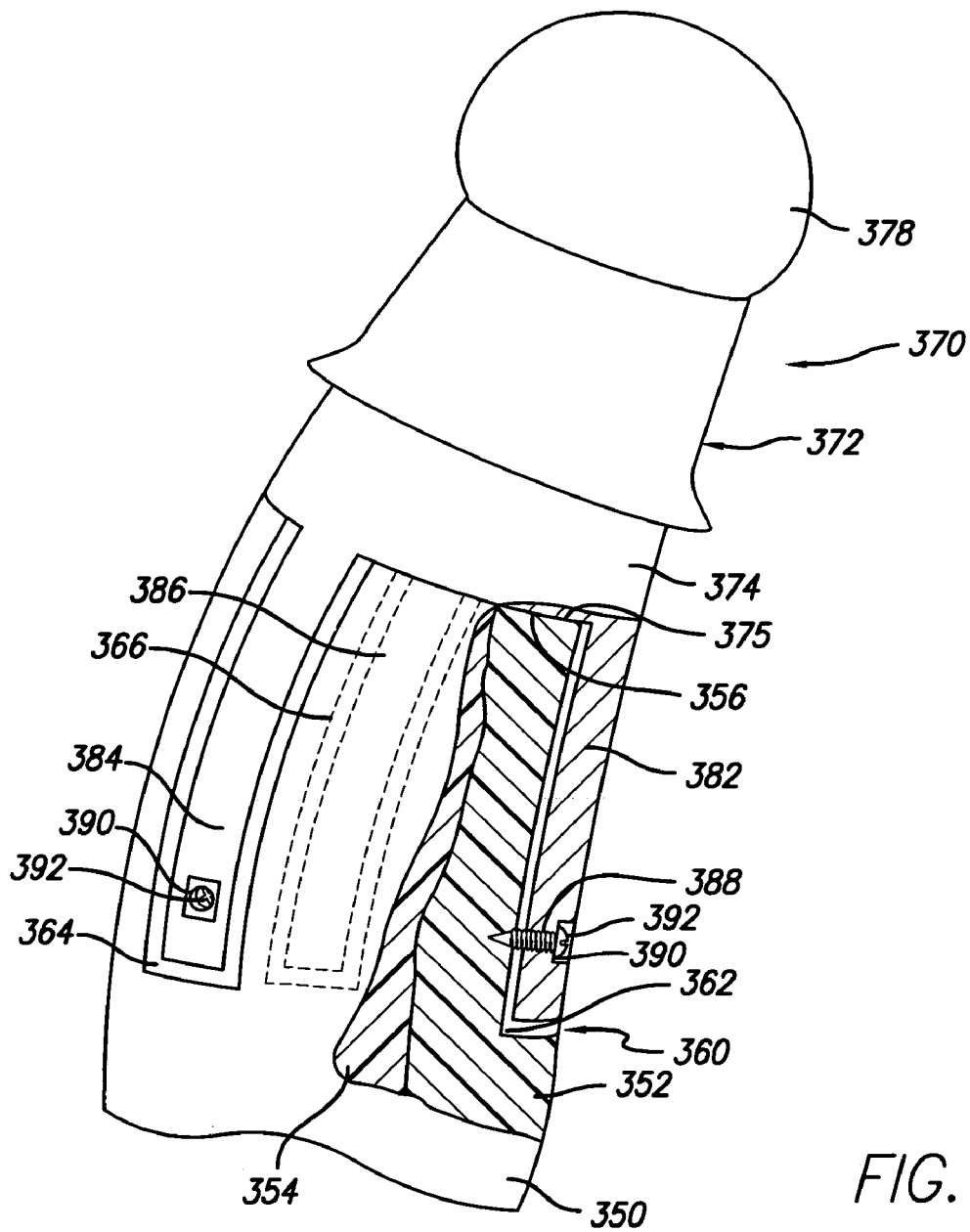
FIG. 19 is an illustration of a further alternative form of implantable brace.

FIG. 19 is an elevation, partially in cross sectional form, illustrating an embodiment in which an implantable brace is formed with an alternative to a lattice structure. In this illustration, a femur 350 has a cortex 352 and cancellous bone 354. The femur 350 may be cut off at a line 356. A prosthetic component 370 is secured to the femur 350. An osteotomy 360 is formed in the cortex 352 to receive portions of the prosthetic component further described below. In the present embodiment, the osteotomy 360 comprises first, second and third substantially axial channels 362, 364 and 366, which may be substantially equiangularly spaced around the periphery of the femur 350. Each of the channels 362, 364 and 366 has a substantially square cross section in a radial plane. The prosthetic component 370 comprises a femoral section 374 of a prosthetic hip joint 372 and a femoral head prosthesis 378. The femur 350 may be scanned and modeled in a manner similar to modeling of the bone 14 of FIG. 3.

The femoral section 374 has first, second and third implantable legs 382, 384 and 386 extending axially therefrom for insertion in the osteotomy 360. The first, second and third implantable legs 382, 384 and 386 are received in the first, second and third channels 362, 364 and 366 respectively. The femoral section 374 and the first, second and third implantable legs 382, 384 and 386 may be made, for example, by casting as described above to fit the femur 350. Other methods could be used. The first, second and third implantable legs 382, 384 and 386 may each have a recess 390 located near an exial end thereof with a central, radially extending apreture 388 through which a surgical screw 392 is inserted into the cortex 352. Each recess 390 has a sufficient depth to assure that a head of the screw 392 will be below and outer surface of its respective implantable legs 382, 384 and 386 so that it will not engage or irritate tissue positioned over the screw 392.

The examples presented herein of a hip joint, a knee joint and the spine are only meant to be illustrative of the present subject matter and are not intended as limiting examples of the implantable braces described herein. These examples are intended to illustrate that the present implantable braces are adaptable to be fixed in virtually any part of the body's bone structure. The shapes of the implantable brace and the osteotomy with which it interacts are not limited to a particular type of shape. Rather, embodiments of the present invention allow structures to be tailored to meet the requirements to suit the judgment and strategy of the surgeon. The present implantable brace provides substantially natural loading to a bone to prevent stress shielding. Additionally, the implantable brace can be fit in an osteotomy to minimize effect on soft tissue and muscles. This will reduce pain produced.

The implantable brace is installed in a manner which will promote natural bone growth for fusing the implantable brace in the body. Many alternative materials may be used to construct an implantable brace. Many different shapes may be provided. Custom made implants may be tailored to particular fractures in particular bones. Prefabricated implants may be used to accommodate a wide variety of common fractures. Accordingly, embodiments of these implantable braces can be varied in many ways. Such variations are not to be regarded as a departure from the spirit and scope of the invention, and all such modifications are intended to be within the scope of the following claims.

What is claimed is:

1. A method for forming an implantable brace implantable in a fractured bone of a patient, said method comprising:
   making a model of a fractured bone of a patient;
   forming an osteotomy design and an osteotomy pattern for the model, the osteotomy design having a depth to receive an envelope of the implantable brace and the osteotomy pattern having a shape to permit implantable portions of the implantable brace to be inserted in an osteotomy without conflict with tissue position;
   cutting the osteotomy design into the model to form an osteotomy model; and
   forming the implantable brace by using the osteotomy model.

2. A method according to claim 1, wherein said making a model step comprises scanning the fractured bone and performing three dimensional printing in accordance with scan data.

3. A method according to claim 2, wherein said forming the implantable brace step is performed by investment casting.

4. A method according to claim 1, further comprising making a transfer template having the osteotomy pattern formed thereon.

5. A method according to claim 4, further comprising performing an osteotomy on the patient utilizing the transfer template to replicate the osteotomy model in the fractured bone of the patient.

6. A method according to claim 5, wherein said making a transfer template comprises cutting guide portions into said template.

7. A method according to claim 6, wherein performing the osteotomy on the patient comprises cutting recesses with a mechanical drill through the transfer template.

8. A method according to claim 6, wherein performing the osteotomy on the patient comprises providing a laser-transparent template and forming the osteotomy by laser.

9. A method according to claim 1, wherein forming an osteotomy pattern comprises accounting for location of tissue adjacent to the bone and forming the pattern in accessible portions of the bone.

10. A method for implanting an implantable brace in an osteotomy in a fractured bone to brace portions of a bone separated by a fracture, said method comprising:
   providing a preformed implantable brace comprising an open framework structure having a contour approximating a contour of a preselected bone, said framework structure having a plurality of members that intersect;
   forming an osteotomy in the bone to a depth to receive the implantable brace below a surface of said bone wherein forming an osteotomy comprises cutting a plurality of channels in registration with said open framework;
   manipulating tissue adjacent to the bone to permit placement of said implantable brace in said osteotomy; and
   placing said implantable brace in said osteotomy to be contained within the volume of the osteotomy, said plurality of channels forming intersections below the surface of the bone.

* * * * *